US011371942B2

(12) United States Patent
Sasahara et al.

(10) Patent No.: US 11,371,942 B2
(45) Date of Patent: Jun. 28, 2022

(54) RAMAN SCATTERED LIGHT ACQUISITION DEVICE, COMPOSITION ANALYSIS DEVICE COMPRISING SAME, AND GAS TURBINE PLANT

(71) Applicant: Mitsubishi Hitachi Power Systems, Ltd., Yokohama (JP)

(72) Inventors: Jun Sasahara, Yokohama (JP); Yosuke Eto, Yokohama (JP); Yosuke Kitauchi, Yokohama (JP); Tsutomu Tomiyama, Yokohama (JP); Yoshihiro Deguchi, Tokushima (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 85 days.

(21) Appl. No.: 16/769,699

(22) PCT Filed: Dec. 5, 2018

(86) PCT No.: PCT/JP2018/044736
§ 371 (c)(1),
(2) Date: Jun. 4, 2020

(87) PCT Pub. No.: WO2019/111953
PCT Pub. Date: Jun. 13, 2019

(65) Prior Publication Data
US 2021/0364440 A1    Nov. 25, 2021

(30) Foreign Application Priority Data
Dec. 7, 2017 (JP) .............................. JP2017-235523

(51) Int. Cl.
*G01N 21/65* (2006.01)
*G01J 3/44* (2006.01)
(Continued)

(52) U.S. Cl.
CPC ............... *G01N 21/65* (2013.01); *F02C 9/22* (2013.01); *G01J 3/4412* (2013.01); *G01N 33/225* (2013.01); *G01N 2021/8578* (2013.01)

(58) Field of Classification Search
CPC ............................. G01N 21/65; G01N 33/225
See application file for complete search history.

(56) References Cited

U.S. PATENT DOCUMENTS

| 2013/0055697 A1* | 3/2013 | Deguchi | ................ | G01N 21/65 |
| | | | | 60/39.24 |
| 2016/0146668 A1 | 5/2016 | Hatahori et al. | | |

(Continued)

FOREIGN PATENT DOCUMENTS

| JP | 06-277173 | 10/1994 |
| JP | 06-294740 | 10/1994 |

(Continued)

OTHER PUBLICATIONS

International Search Report dated Feb. 12, 2019 in International (PCT) Application No. PCT/JP2018/044736 with English translation.

(Continued)

*Primary Examiner* — Hina F Ayub
(74) *Attorney, Agent, or Firm* — Wenderoth, Lind & Ponack, L.L.P.

(57) ABSTRACT

A Raman scattered light acquisition device includes an emitting optical system configured to guide excitation light into a fluid, a scattered light window configured to define a part of a flow path of the fluid and through which Raman scattered light from the fluid irradiated with the excitation light passes, and a scattered light receiving device having a light receiving surface receiving Raman scattered light passed through the scattered light window. The scattered light window and the light receiving surface of the scattered light receiving device are disposed at a position in which (Continued)

they are separated from an optical axis in the fluid in a radial direction within a range in which an optical path of the excitation light in the fluid is present in an optical axis direction in which the optical axis in the fluid which is an optical axis of the excitation light in the fluid extends.

13 Claims, 5 Drawing Sheets

(51) Int. Cl.
*F02C 9/22* (2006.01)
*G01N 33/22* (2006.01)
*G01N 21/85* (2006.01)

(56) References Cited

U.S. PATENT DOCUMENTS

2016/0218809 A1* 7/2016 Imanishi ............... H04B 10/071
2017/0045454 A1* 2/2017 Sharma .................. G01N 21/65

FOREIGN PATENT DOCUMENTS

| | | |
|---|---|---|
| JP | 09-230397 | 9/1997 |
| JP | 2002-286644 | 10/2002 |
| JP | 2005-024250 | 1/2005 |
| JP | 2011-080768 | 4/2011 |
| JP | 2015-072179 | 4/2015 |
| JP | 2016-029343 | 3/2016 |
| JP | 2016-036431 | 3/2016 |
| JP | 2016-080349 | 5/2016 |
| WO | 2014/082957 | 6/2014 |
| WO | 2015/005075 | 1/2015 |

OTHER PUBLICATIONS

Written Opinion of the International Searching Authority dated Feb. 12, 2019 in International (PCT) Application No. PCT/JP2018/044736 with English translation.

* cited by examiner

| | AMOUNT OF RAMAN SHIFT (cm$^{-1}$) | WAVELENGTH AT TIME OF INCIDENCE AT 405 nm (nm) |
|---|---|---|
| $N_2$ | 2330 | 447.2 |
| CO | 2195 | 444.5 |
| $CO_2$ | 1360 | 428.6 |
| $H_2O$ | 3660 | 475.5 |
| $CH_4$ | 2916 | 459.2 |
| $H_2$ | 4360 | 491.9 |
| $O_2$ | 1580 | 432.7 |

RAMAN SCATTERED LIGHT ACQUISITION DEVICE, COMPOSITION ANALYSIS DEVICE COMPRISING SAME, AND GAS TURBINE PLANT

TECHNICAL FIELD

The present invention relates to a Raman scattered light acquisition device which acquires Raman scattered light from a fluid, a composition analysis device including the same, and a gas turbine plant.

Priority is claimed on Japanese Patent Application No. 2017-235523, filed Dec. 7, 2017, the content of which is incorporated herein by reference.

BACKGROUND ART

As a method of analyzing a composition of a fluid, there are methods of analyzing Raman scattered light from a fluid irradiated with excitation light by irradiating the fluid with excitation light. Examples of devices which perform these methods include the composition analysis device described in Patent Document 1 which will be described below. The composition analysis device includes a measurement cell having a fluid flowing therein, a laser oscillator which oscillates laser light which is excitation light, an emission optical system which irradiates the fluid in the measurement cell with laser light from the laser oscillator, a light receiving optical system which receives Raman scattered light from the fluid irradiated with laser light, an optical fiber which receives the Raman scattered light condensed using the light receiving optical system, and an analyzing device which is configured to analyze light received using the optical fiber.

An optical axis of the emission optical system extends in a flow perpendicular direction perpendicular to a main flow direction of the fluid flowing in the measurement cell. The emission optical system is provided on one side in the flow perpendicular direction with reference to the measurement cell. An optical axis of the light receiving optical system coincides with the optical axis of the emission optical system. Thus, the optical axis of the light receiving optical system also extends in the flow perpendicular direction. The light receiving optical system is provided on the other side in the flow perpendicular direction with reference to the measurement cell.

CITATION LIST

Patent Document

[Patent Document 1]
Japanese Unexamined Patent Application, First Publication No. 2015-072179

SUMMARY OF INVENTION

Technical Problem

In the composition analysis industry, it is desired to reduce the size of a composition analysis device.

Therefore, an object of the present invention is to provide a technique capable of reducing a size of a device.

Solution to Problem

A Raman scattered light acquisition device as an aspect associated with the invention for achieving the above object includes: an emission optical system which is configured to guide excitation light from a light emission unit into a fluid; a scattered light window which is configured to define a part of a flow path of the fluid and through which Raman scattered light from the fluid irradiated with the excitation light passes; and a scattered light receiving device which has a light receiving surface receiving the Raman scattered light which has passed through the scattered light window, wherein the scattered light window and the light receiving surface of the scattered light receiving device are disposed at positions in which the scattered light window and the light receiving surface are separated from an optical axis in the fluid in a radial direction which is a direction perpendicular to the optical axis in the fluid within a range in which an optical path of the excitation light in the fluid is present in an optical axis direction in which the optical axis in the fluid which is an optical axis of the excitation light in the fluid extends, and the light receiving surface faces a radially inward side which is a side in proximity to the optical axis in the fluid in the radial direction.

In this aspect, the light receiving surface of the scattered light receiving device is arranged at a position in which the light receiving surface is separated from a scattered light generation region in the fluid in the direction perpendicular to the optical axis in the fluid. For this reason, in this aspect, the light receiving surface of the scattered light receiving device can be brought into proximity to the scattered light generation region in the fluid. Thus, in this aspect, it is possible to reduce a size of the Raman scattered light acquisition device.

Also, in this aspect, the light receiving surface of the scattered light receiving device can be brought into proximity to the scattered light generation region in the fluid. Thus, the light receiving surface of the scattered light receiving device can receive Raman scattered light with little attenuation. For this reason, in this aspect, the condensing optical system configured to condense scattered light which has passed through the scattered light window can be omitted. Thus, in this aspect, also from this viewpoint, it is possible to reduce the size of the Raman scattered light acquisition device.

Here, in the Raman scattered light acquisition device, a light receiving surface optical axis which is the optical axis in the light receiving surface of the scattered light receiving device may be perpendicular to the optical axis in the fluid.

In this aspect, it is possible to efficiently receive Raman scattered light which travels in the direction perpendicular to the optical axis in the fluid with a short optical path length.

Also, in any of the above Raman scattered light acquisition devices, the inner surface in the scattered light window which is configured to define the flow path of the fluid and the outer surface opposite to the inner surface may be both parallel to the optical axis in the fluid.

In this aspect, the Raman scattered light emitted in the direction perpendicular to the optical axis in the fluid in the Raman scattered light emitted from the fluid can be made to travel in a straight line. For this reason, it is possible to shorten an optical path length of scattered light from the optical axis in the fluid to the light receiving surface of the scattered light receiving device.

In any of the above Raman scattered light acquisition devices, the emission optical system may include an emission optical fiber cable through which the excitation light from the light emission unit passes and a changer which is configured to change a direction of the excitation light emitted from the emission optical fiber cable. In this case, an emission surface optical axis which is an optical axis in an emission surface of the emission optical fiber cable which emits the excitation light may extend in a direction intersecting the optical axis in the fluid. The emission surface of the emission optical fiber cable and the changer may be arranged on one side in the optical axis direction with reference to the light receiving surface of the scattered light receiving device and the changer may cause the optical axis of the excitation light emitted from the emission optical fiber cable to coincide with the optical axis in the fluid.

In this aspect, a width of the Raman scattered light acquisition device in the optical axis direction can be reduced.

Also, in the Raman scattered light acquisition device having the emission optical fiber cable, the emission surface optical axis may be perpendicular to the optical axis in the fluid.

In this aspect, the width of the Raman scattered light acquisition device in the optical axis direction can be made smaller.

Any of the above Raman scattered light acquisition devices may include: a light shielding member through which the excitation light and the Raman scattered light do not pass; and a heating optical fiber cable using which the light shielding member is irradiated with excitation light. In this case, the light shielding member may be in contact with an outer surface of the scattered light window on the light receiving surface side.

In this aspect, it is possible to heat the scattered light window using energy of the excitation light. For this reason, in this aspect, it is possible to remove foreign matter adhered to the inner surface of the scattered light window and to prevent adhering of foreign matter to the scattered light window.

Also, since electricity is not used to heat the scattered light window in this aspect, an explosion-proofing treatment necessary for components for heating the scattered light window, that is, for the heating optical fiber cable and the heating light shielding member can be omitted.

In the Raman scattered light acquisition device including the light shielding member, a cavity which extends along the outer surface of the scattered light window may be formed inside the light shielding member and the heating optical fiber cable may emit into the cavity of the light shielding member.

Since the light shielding member can be irradiated with all of the excitation light in this aspect, it is possible to increase the efficiency of converting light energy of the excitation light into heat energy.

Any of the above Raman scattered light acquisition devices may include: an excitation light receiving optical system which is configured to receive the excitation light from the emission optical system; and a determination unit which is configured to determine an abnormality of an excitation light optical system constituted of a plurality of members through which the excitation light passes in accordance with a difference between the light intensity of the excitation light from the light emission unit and the light intensity of the excitation light received by the excitation light receiving optical system.

In this aspect, it is possible to recognize an abnormality in the excitation light optical system constituted of the plurality of members through which the excitation light passes.

In the Raman scattered light acquisition device including the excitation light receiving optical system, the excitation light receiving optical system may be arranged on a side opposite to the emission optical system in the optical axis direction with reference to the light receiving surface of the scattered light receiving device.

Any of the above Raman scattered light acquisition devices may include the light emission unit.

A composition analysis device as an aspect associated with the invention for achieving the above object includes: any of the above Raman scattered light acquisition devices; and an analyzing device which is configured to analyze a composition of the fluid on the basis of an output from the scattered light receiving device.

In this aspect, it is possible to analyze the composition of the fluid.

Here, in the composition analysis device, a distance in the radial direction from the optical axis in the fluid to the light receiving surface of the scattered light receiving device may be equal to or less than a distance in which an amount of the Raman scattered light received by the scattered light receiving device is a minimum amount of light in which the analyzing device is able to analyze the composition of the fluid.

A gas turbine plant as an aspect associated with the invention for achieving the above object includes: any of the above composition analysis devices; a fuel gas line through which a fuel gas as the fluid flows; a fuel adjustment valve which is configured to adjust a flow rate of the fuel gas flowing through the fuel gas line; a gas turbine configured to be driven through combustion of the fuel gas from the fuel gas line; and a control device which is configured to instruct a degree of opening of the fuel adjustment valve. The Raman scattered light acquisition device is attached to the fuel gas line. The analyzing device is configured to analyze a composition of the fuel gas flowing in the fuel gas line. The control device is configured to determine the degree of opening of the fuel adjustment valve in accordance with the analysis results in the analyzing device and instruct the degree of opening to the fuel adjustment valve.

Advantageous Effects of Invention

According to the present invention, it is possible to reduce the size of a device.

DESCRIPTION OF EMBODIMENTS

An embodiment of a composition analysis device associated with the present invention and an embodiment of a gas turbine plant including the composition analysis device will be described below with reference to the drawings.

First Embodiment

A first embodiment of the composition analysis device associated with the present invention and the embodiment of the gas turbine plant including the composition analysis device will be described with reference to FIGS. 1 to 5.

Figure 5:
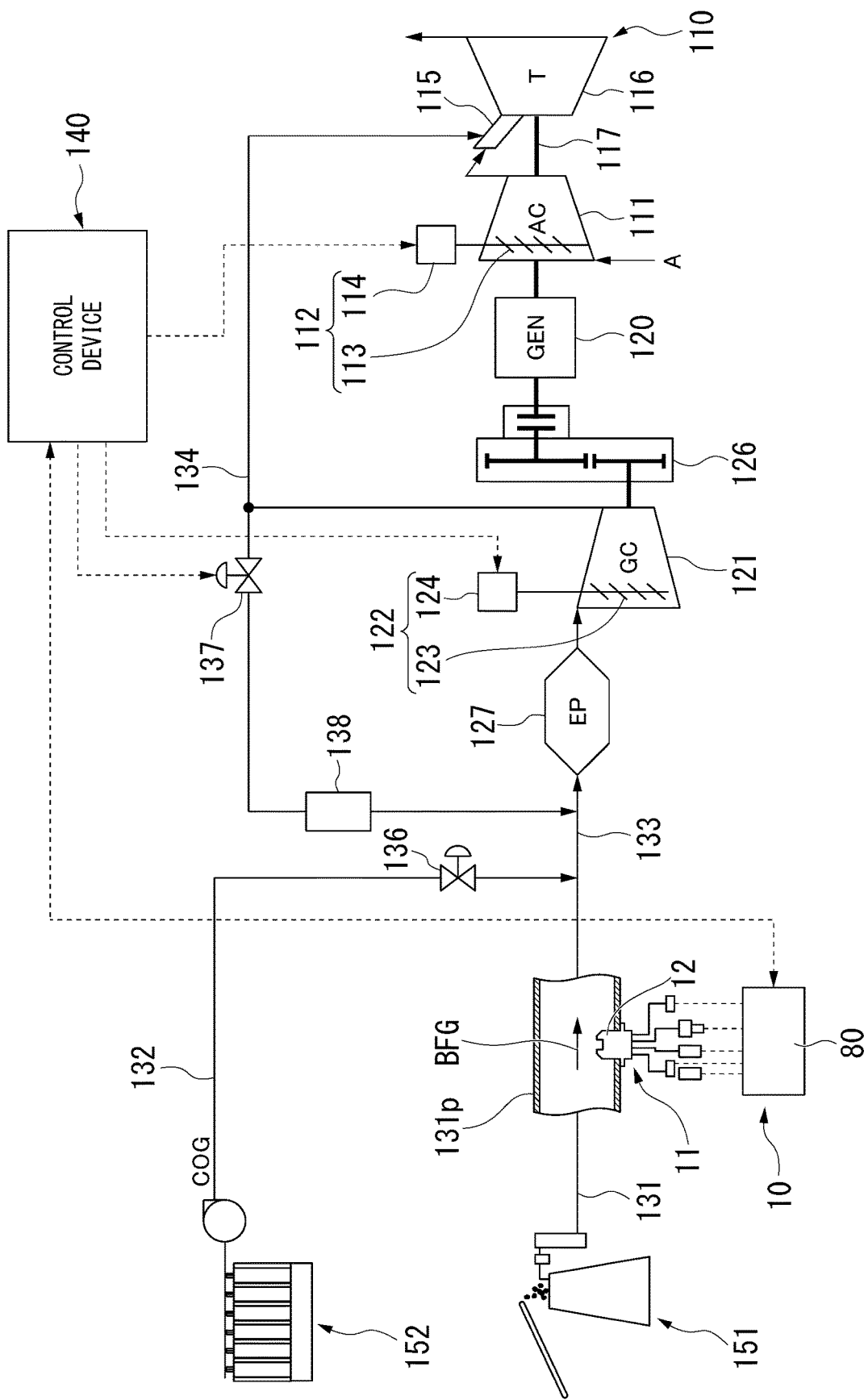
FIG. 5 is a system diagram of a gas turbine plant according to an embodiment of the present invention.

A fluid analyzed by the composition analysis device in this embodiment is, for example, a fuel gas flowing in a pipe. To be specific, as illustrated in FIG. 5, the fluid is a fuel gas for driving a gas turbine of the gas turbine plant.

The gas turbine plant includes a gas turbine 110, an electric generator 120 which generates electricity through driving of the gas turbine 110, a gas compressor 121 which compresses a fuel gas through driving of the gas turbine 110, a composition analysis device 10 which analyzes a composition of a gas to be supplied to the gas turbine 110, and a control device 140 which controls a state or the like of the gas turbine 110.

The gas turbine 110 includes an air compressor 111 which compresses air A to generate compressed air, a combustor 115 which combusts a fuel gas in the compressed air to generate a high-temperature combustion gas, and a turbine 116 which is driven using the combustion gas.

The air compressor 111 includes a compressor rotor, a compressor casing which rotatably covers the compressor rotor, and an intake amount adjuster 112 which adjusts an amount of intake of the air A. The intake amount adjuster 112 includes an inlet guide vane 113 provided on a suction port side of the compressor casing and a guide vane driver 114 which changes a degree of opening of the inlet guide vane 113.

The turbine 116 includes a turbine rotor which rotates using a combustion gas and a turbine casing which rotatably covers the turbine rotor. The compressor rotor and the turbine rotor are connected to each other and integrally formed to form a gas turbine rotor 117.

The electric generator 120 includes an electric generator rotor and an electric generator casing which rotatably covers the electric generator rotor. The electric generator rotor is connected to the gas turbine rotor 117. For this reason, if the gas turbine rotor 117 rotates, the electric generator rotor also rotates integrally.

The gas compressor 121 includes a compressor rotor, a compressor casing which rotatably covers the compressor rotor and an intake gas amount adjuster 122 which adjusts an amount of intake of a fuel gas. The intake gas amount adjuster 122 includes an inlet guide vane 123 provided on a suction port side of the compressor casing and a guide vane driver 124 which changes a degree of opening of the inlet guide vane 123. The compressor rotor of the gas compressor 121 is mechanically connected to the electric generator rotor or the gas turbine rotor 117 via a speed reducer 126. A discharge port of the gas compressor 121 is connected to the combustor 115 through a high-pressure fuel gas line 134.

A fuel gas is supplied from a steel mill 151 and a coke plant 152 to the gas turbine plant. The steel mill 151 generates a blast furnace gas (BFG) as a low-calorie fuel gas from a blast furnace in the steel mill 151. A BFG line 131 through which a BFG flows is connected to the blast furnace. The coke plant 152 generates a coke oven gas (COG) as a high-calorie fuel gas from a coke oven in the coke plant 152. A COG line 132 through which a COG flows is connected to the coke oven. A COG adjustment valve 136 which adjusts a flow rate of the COG is provided in the COG line 132. The BFG line 131 and the COG line 132 are joined to form a low-pressure fuel gas line 133. Any of an independent BFG, an independent COG, and a mixture of a BFG and a COG flows through the low-pressure fuel gas line 133. The low-pressure fuel gas line 133 is connected to the suction port of the gas compressor 121. An electrostatic precipitator (EP) 127 which collects dust and the like in a gas passing through the low-pressure fuel gas line 133 is provided in the low-pressure fuel gas line 133. A gas such as a Linz-Donawitz converter gas (LDG) which is a gas generated in a converter in the middle of the BFG line 131 may be mixed in in the BFG line 131 in some cases.

The gas turbine plant includes the BFG line 131, the COG line 132, the low-pressure fuel gas line 133, the COG adjustment valve 136, and the electrostatic precipitator 127 which have been described above. The gas turbine plant further includes a fuel gas circulation line 135, a circulation amount adjustment valve 137, and a gas cooler 138. A first end of the fuel gas circulation line 135 is connected to the high-pressure fuel gas line 134. Furthermore, a second end of the fuel gas circulation line 135 is connected to a position of the low-pressure fuel gas line 133 upstream of the electrostatic precipitator 127. The gas cooler 138 and the circulation amount adjustment valve 137 are provided in the fuel gas circulation line 135.

The gas cooler 138 cools a gas flowing through the fuel gas circulation line 135. If a degree of opening of the circulation amount adjustment valve 137 is changed and a flow rate of the gas flowing through the fuel gas circulation line 135 is changed, a flow rate of a gas supplied to the combustor 115 is also changed. For this reason, the circulation amount adjustment valve 137 functions as a fuel adjustment valve which adjusts a flow rate of a fuel gas to be supplied to the combustor 115. Furthermore, the intake gas amount adjuster 122 of the gas compressor 121 described above also functions as a fuel adjustment valve. The composition analysis device 10 is provided in the BFG line 131. The composition analysis device 10 analyzes a composition of a BFG flowing through the BFG line 131. Here, although the composition analysis device 10 is provided in the BFG line 131, the composition analysis device 10 may be provided in the low-pressure fuel gas line 133 or the COG line 132 in some cases.

The control device 140 controls a degree of opening of the circulation amount adjustment valve 137, a degree of opening of the inlet guide vane 113, or the like in accordance with a load command from the outside, a composition of a BFG which is a gas analyzed by the composition analysis device 10, or the like. Furthermore, the control device 140 also controls a degree of opening of the COG adjustment valve 136 in accordance with a load command from the outside, a composition of a gas G (a BFG) analyzed by the composition analysis device 10, or the like in some cases.

Figure 1:
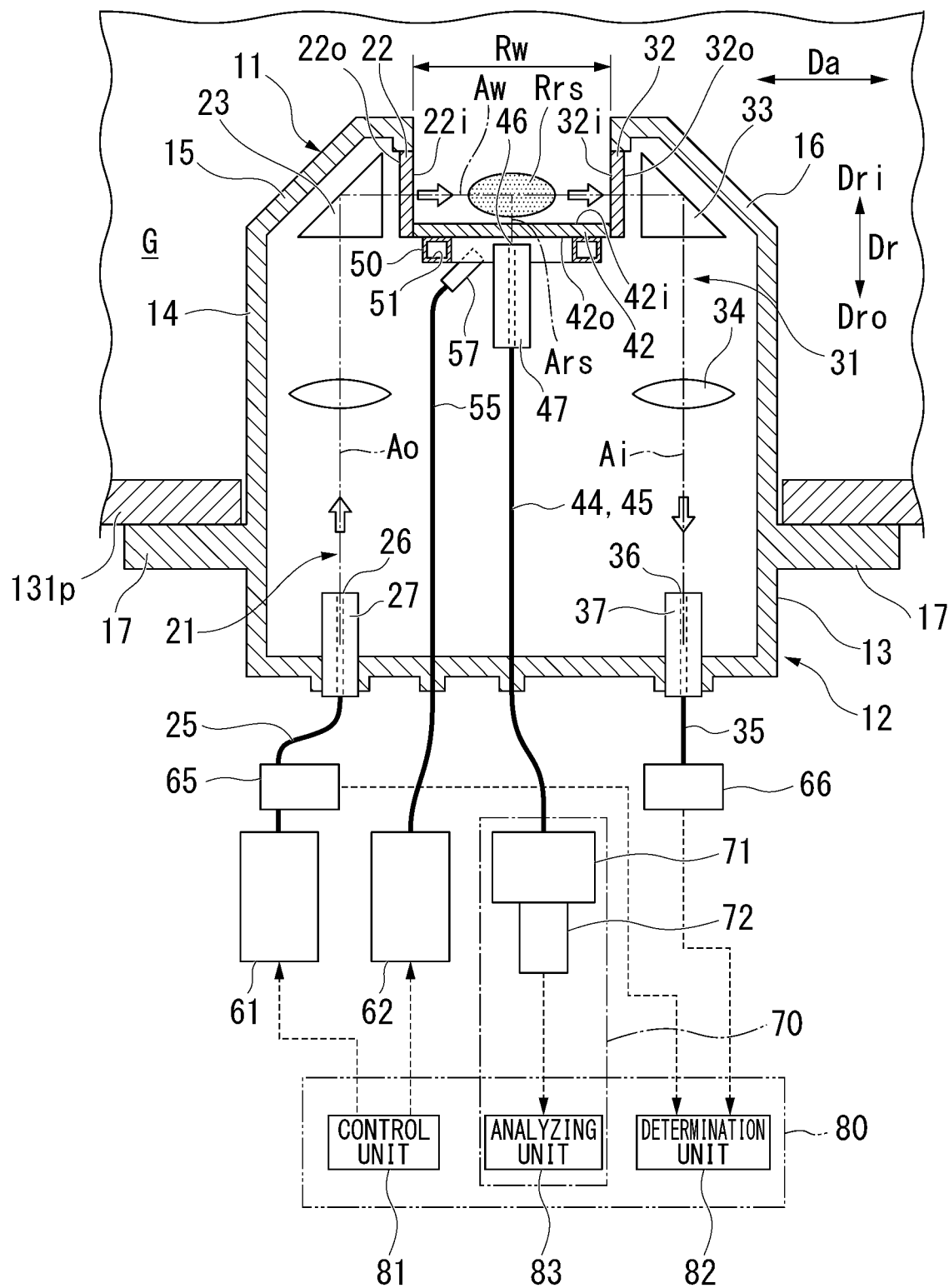
FIG. 1 is a schematic diagram illustrating a constitution of a composition analysis device according to a first embodiment of the present invention.

As illustrated in FIG. 1, the composition analysis device 10 includes a Raman scattered light acquisition device 11 which acquires Raman scattered light from a fluid G irradiated with laser light which is excitation light and an analyzing device 70 which analyzes a composition of the fluid G on the basis of the Raman scattered light acquired by the Raman scattered light acquisition device 11.

Hereinafter, the Raman scattered light may also be simply referred to as "scattered light" in some cases.

The Raman scattered light acquisition device 11 includes a scattered light acquisition head 12, an analyzing laser oscillator (a light emission unit) 61, a heating laser oscillator 62, a control unit 81 which controls the laser oscillators 61 and 62, two determination units 65 and 66 which determine the intensity of laser light, and a determination unit 82 which determines a state of the scattered light acquisition head 12 in accordance with outputs from the two determination units 65 and 66.

The analyzing laser oscillator 61 oscillates laser light with which the fluid G is irradiated. The heating laser oscillator 62 oscillates laser light which heats a part of the scattered light acquisition head 12.

The scattered light acquisition head 12 includes a head casing 13, an emission optical system 21 which guides laser light from the analyzing laser oscillator 61 which is a light emission unit into the fluid G, a laser light receiving optical system (an excitation light receiving optical system) 31 which receive laser light which has passed through the fluid G, a scattered light window 42 which defines a part of a flow path of the fluid G and through which Raman scattered light from the fluid G passes, a scattered light receiving device 44 which receives the Raman scattered light which has passed through the scattered light window 42, a light shielding member 50 in contact with the scattered light window 42, and a heating optical fiber cable 55 which guides heating laser light to the light shielding member 50.

The emission optical system 21 includes an emission optical fiber cable 25 through which laser light from the analyzing laser oscillator 61 passes, an emission prism (a changer) 23 which changes a direction of laser light emitted from the emission optical fiber cable 25, and a laser emission window 22 which defines a part of the flow path of the fluid G and through which laser light passes.

The emission optical fiber cable 25 has an optical fiber (not shown), a covering member (not shown) which covers the outer circumference of the optical fiber, and a sleeve 27 which covers an outer circumference of an end of the optical fiber. The sleeve 27 of the emission optical fiber cable 25 on an emission side thereof is attached to the head casing 13.

The emission prism 23 perpendicularly bends an optical axis of laser light emitted from the emission optical fiber cable 25. In other words, the emission prism 23 makes an optical axis of laser light which has passed through the emission prism 23 perpendicular to an optical axis Ao of an emission surface of the emission optical fiber cable 25. The optical axis Ao of the emission surface is an optical axis of an emission surface 26 from which laser light is emitted through the emission optical fiber cable 25. The emission prism 23 is arranged in the head casing 13 and is fixed to the head casing 13.

Laser light whose direction is changed through the emission prism 23 passes through the laser emission window 22. An inner surface 22i in the laser emission window 22 which defines the flow path of the fluid G and an outer surface 22o in the laser emission window 22 on the emission prism 23 side are both perpendicular to an optical axis of laser light which has passed through the emission prism 23. For this reason, an optical axis of laser light which has passed through the emission prism 23 and which does not reach the laser emission window 22 coincides with an optical axis Aw in a fluid which is an optical axis of laser light which has passed through the laser emission window 22 and has reached the fluid G. The laser emission window 22 is fixed to the head casing 13.

The emission optical system 21 described above does not have a condensing optical system. However, a condensing optical system which condenses laser light emitted from the emission optical fiber cable 25 into the fluid G may be provided.

The laser light receiving optical system (the excitation light receiving optical system) 31 includes a laser receiving window 32 which defines a part of the flow path of the fluid G and through which laser light passes, a light receiving prism 33 which changes a direction of laser light which has passed through the laser receiving window 32, a laser receiving optical fiber cable 35 on which laser light which has passed through the light receiving prism 33 is incident, and a condensing optical system 34 which condenses laser light which has passed through the light receiving prism 33 on a light receiving surface 36 of the laser receiving optical fiber cable 35.

The laser receiving window 32 is arranged above the optical axis Aw in the fluid. The inner surface 32i in the laser receiving window 32 which defines the flow path of the fluid G and the outer surface 32o in the laser receiving window 32 on the light receiving prism 33 side are both perpendicular to the optical axis Aw in the fluid. For this reason, an optical axis of laser light which has passed through the laser receiving window 32 coincides with the optical axis Aw in the fluid. The laser receiving window 32 is fixed to the head casing 13.

The light receiving prism 33 perpendicularly bends an optical axis of laser light which has passed through the laser receiving window 32. In other words, the light receiving prism 33 makes the optical axis of the laser light which has passed through the light receiving prism 33 perpendicular to the optical axis Aw in the fluid. The light receiving prism 33 is arranged in the head casing 13 and is fixed to the head casing 13.

The laser receiving optical fiber cable 35 has an optical fiber (not shown), a covering member (not shown) which covers an outer circumference of the optical fiber, and a sleeve 37 which covers an outer circumference of an end of the optical fiber. The sleeve 37 of the laser receiving optical fiber cable 35 on a light receiving side thereof is attached to the head casing 13.

A light receiving surface optical axis Ai of the laser receiving optical fiber cable 35 coincides with the optical axis of the laser light which has passed through the light receiving prism 33. The light receiving surface optical axis Ai is an optical axis of the light receiving surface 36 in the laser receiving optical fiber cable 35 which receives the laser light from the light receiving prism 33.

Hereinafter, a direction in which the optical axis Aw in the fluid extends is assumed to be an "optical axis direction Da." Furthermore, a direction in which the light receiving surface 36 of the laser receiving optical fiber cable 35 is present with respect to the optical axis Aw in the fluid among directions perpendicular to the optical axis Aw in the fluid is assumed to be a "radial direction Dr." In this radial direction Dr, a side closer to the optical axis Aw in the fluid is assumed to be a radially inward side Dri and an opposite side is assumed to be a radially outward side Dro.

As described above, scattered light passes through the scattered light window 42 and laser light is reflected by the scattered light window 42. The scattered light window 42 is arranged at a position in which the scattered light window 42 is separated from the optical axis Aw in the fluid in the radial direction Dr within the range Rw in which the optical path of the laser light in the fluid G is present in the optical axis direction Da. The inner surface 42i in the scattered light window 42 which defines the flow path of the fluid G and the outer surface 42o which is a surface in the scattered light window 42 opposite to the inner surface 42i are both parallel to the optical axis Aw in the fluid. The inner surface 42i of the scattered light window 42 faces the radially inward side Dri and the outer surface 42o of the scattered light window 42 faces the radially outward side Dro.

The scattered light receiving device 44 has a scattered light optical fiber cable 45 configured to receive scattered light which has passed through the scattered light window 42. A light receiving surface 46 of the scattered light optical fiber cable 45 is arranged at a position in which the light receiving surface 46 is separated from the optical axis Aw in the fluid in the radial direction Dr within the range Rw in which the optical path of the laser light in the fluid G is present in the optical axis direction Da, as in the scattered light window 42. Here, the light receiving surface 46 is located on the radially outward side Dro with respect to the scattered light window 42 and faces the radially inward side Dri. The scattered light optical fiber cable 45 has an optical fiber (not shown), a covering member (not shown) which covers an outer circumference of the optical fiber, and a sleeve 47 which covers an outer circumference of an end of the optical fiber. The sleeve 47 of the scattered light optical fiber cable 45 on a light receiving side thereof is attached to the head casing 13.

The emission surface 26 of the emission optical fiber cable 25, the light receiving surface 36 of the laser receiving optical fiber cable 35, and the light receiving surface 46 of the scattered light optical fiber cable 45 are all arranged at positions in which they are separated from the optical axis Aw in the fluid in the radial direction Dr. Furthermore, the emission surface 26 of the emission optical fiber cable 25, the light receiving surface 36 of the laser receiving optical fiber cable 35, and the light receiving surface 46 of the scattered light optical fiber cable 45 are all surfaces parallel to the optical axis Aw in the fluid. Thus, the emission surface optical axis Ao of the emission optical fiber cable 25, the light receiving surface optical axis Ai of the laser receiving optical fiber cable 35, and a light receiving surface optical axis Ars of the scattered light optical fiber cable 45 are all parallel to each other and are perpendicular to the optical axis Aw in the fluid.

Figure 2:
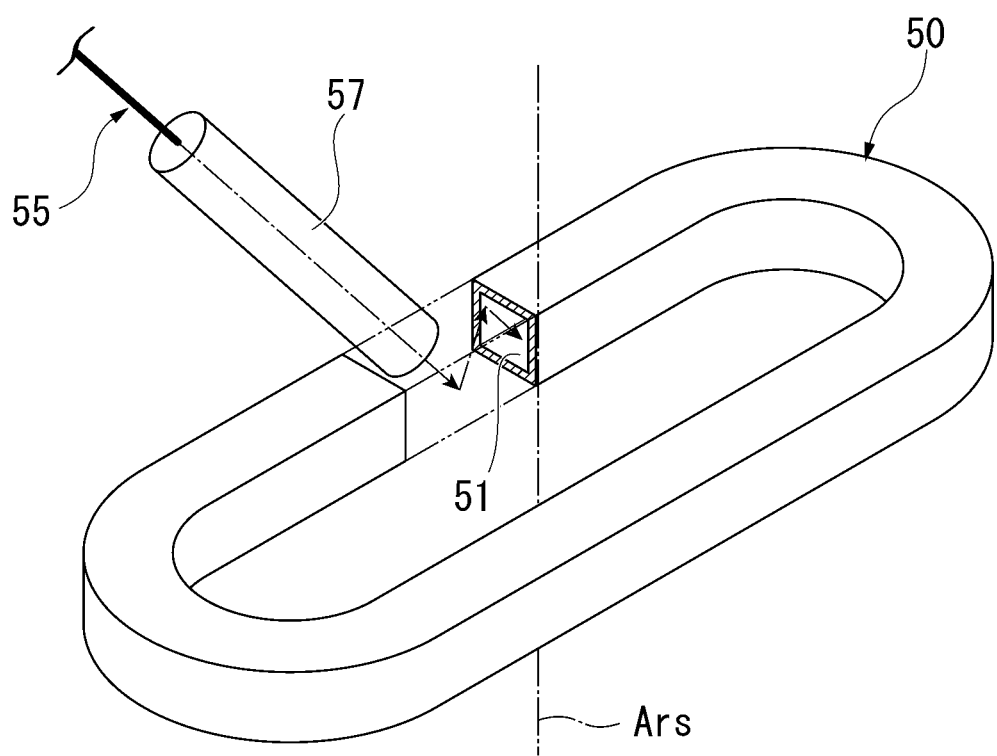
FIG. 2 is a perspective view of a light heat shield member and a heating optical fiber according to the first embodiment of the present invention.

The light shielding member 50 is adhered to the outer surface 42o of the scattered light window 42 with an adhesive or the like. The light shielding member 50 is formed of a member through which laser light or Raman scattered light does not pass, which easily absorbs the energy of the laser light or the Raman scattered light, and which has good thermal conductivity. To be specific, the light shielding member 50 is formed of copper, brass, or an alloy containing these. As illustrated in FIGS. 1 and 2, an outer shape of the light shielding member 50 is annular. An inside of this annular shape forms an optical path through which scattered light passes. An annular cavity 51 which extends along the outer surface 42o of the scattered light window 42 and matches the outer shape of the light shielding member 50 is formed inside the light shielding member 50.

The heating optical fiber cable 55 has an optical fiber (not shown), a covering member (not shown) which covers an outer circumference of the optical fiber, and a sleeve 57 which covers an outer circumference of an end of the optical fiber. The sleeve 57 of the heating optical fiber cable 55 on an emission side thereof is attached to the light shielding member 50. To be specific, the sleeve 57 of the heating optical fiber cable 55 is attached to the light shielding member 50 from a direction inclined with respect to an inner surface of the cavity of the light shielding member 50 and the outer surface 42o of the scattered light window 42 so that laser light from the heating optical fiber cable 55 is emitted into the cavity 51 of the light shielding member 50.

The head casing 13 has a main body section 14 and two protrusion sections 15 and 16. A part of the sleeve 27 of the emission optical fiber cable 25, a part of the sleeve 37 of the laser receiving optical fiber cable 35, the condensing optical system 34, the sleeve 47 of the scattered light optical fiber cable 45, the light shielding member 50, and the sleeve 57 of the heating optical fiber cable 55 are accommodated in the main body section 14 and they are attached to the main body section 14. An attachment flange 17 configured to attach the head casing 13 to a pipe 131p through which a fluid G flows is provided in the main body section 14. The pipe 131p is a pipe which constitutes the BFG line 131 through which a BFG flows. The two protrusion sections 15 and 16 protrude from the main body section 14 in a direction in which the two protrusion sections 15 and 16 become further away from the attachment flange 17. The two protrusion sections 15 and 16 are separated from each other in a direction perpendicular to a direction in which the protrusion sections 15 and 16 protrude from the main body section 14. The emission prism 23 is accommodated in a first protrusion section 15 of the two protrusion sections 15 and 16 and the emission prism 23 is attached to the first protrusion section 15. Furthermore, the light receiving prism 33 is accommodated in a second protrusion section 16 which is the other protrusion section of the two protrusion sections 15 and 16 and the light receiving prism 33 is attached to the second protrusion section 16. The laser emission window 22 is attached to a surface in the first protrusion section 15 facing the second protrusion section 16. Furthermore, the laser receiving window 32 is attached to a surface in the second protrusion section 16 facing the first protrusion section 15. Thus, the direction in which the two protrusion sections 15 and 16 are separated is the optical axis direction Da. Furthermore, a direction in which the two protrusion sections 15 and 16 protrude from the main body section 14 is the radial direction Dr. The scattered light window 42 is attached to a surface of the main body section 14 on the radially inward side Dri thereof between the two protrusion sections 15 and 16 in the optical axis direction Da.

In a state in which the head casing 13 is attached to the pipe 131p using the attachment flange 17, the first protrusion section 15, the second protrusion section 16, and a portion of the main body section 14 on the radially inward side Dri are all located in the pipe 131p.

An emitted light determination unit 65 which is one determination unit of the two determination units 65 and 66 determines the intensity of laser light oscillated from the analyzing laser oscillator 61 or laser light passing through the emission optical fiber cable 25. A light receiving determination unit 66 which is the other determination unit of the two determination units 65 and 66 determines the intensity of laser light which has passed through the laser receiving optical fiber cable 35.

As described above, the determination unit 82 determines a state of the scattered light acquisition head 12 in accordance with outputs from the two determination units 65 and 66. To be specific, for example, when a difference between the light intensity determined by the emitted light determination unit 65 and the light intensity determined by the light receiving determination unit 66 is a predetermined value or more, it is determined that the scattered light acquisition head 12 is abnormal. Examples of a form of an abnormality determined by the determination unit 82 include the following forms. There is an abnormal form of a direction of the optical axis Ao of the emission surface of an emitted light optical fiber cable and a direction of the light receiving surface optical axis Ai of the laser receiving optical fiber cable 35. Furthermore, there is an abnormal form of the arrangement and direction of the emission prism 23 and the light receiving prism 33. In addition, there is an abnormal form of the analyzing laser oscillator 61. There is also a form in which the laser emission window 22 and the laser receiving window 32 are dirty.

The analyzing device 70 includes a spectroscope 71 which disperses scattered light received by the scattered light optical fiber cable 45 into light for each of a plurality of wavelength bands, a camera 72 which outputs light for each of the plurality of wavelength bands dispersed using the spectroscope 71 as a digital signal, and an analyzing unit 83 which analyzes a composition in the fluid G on the basis of the digital signal associated with the light for each of the plurality of wavelength bands.

A computer 80 has, as functional constitutions, the control unit 81, the determination unit 82 and the analyzing unit 83 described above. All of the control unit 81, the determination unit 82, and the analyzing unit 83 are constituted to have a program stored in a memory or the like of the computer 80 and a central processing unit (CPU) which executes this program.

As illustrated in FIG. 5, the control device 140 can communicate with the computer 80. For example, the control device 140 outputs (displays) the determination result using the determination unit 82. Furthermore, the control device 140 controls a degree of opening of the circulation amount adjustment valve 137, a degree of opening of the inlet guide vane 113, and in some cases, a degree of opening of the COG adjustment valve 136 and the like in accordance with the analysis result using the analyzing unit 83.

An operation of the composition analysis device 10 described above will be described below.

The laser light oscillated from the analyzing laser oscillator 61 is incident on the emission optical fiber cable 25 and passes through the emission optical fiber cable 25. The optical axis of the laser light emitted from the emission optical fiber cable 25 is bent perpendicularly through the emission prism 23. The fluid G in the pipe 131p is irradiated with the laser light whose optical axis is bent through the laser emission window 22.

If the fluid G is irradiated with excitation light, Raman scattered light with a specific wavelength is generated for each component in the fluid G. In other words, when the fluid G is irradiated with laser light with a predetermined wavelength, as illustrated in FIG. 3, Raman scattered light whose wavelength is shifted from a wavelength of laser light by a specific amount of shift is generated for each component in the fluid G.

Scattered light is received by the scattered light optical fiber cable 45 through the scattered light window 42. The scattered light is guided to the spectroscope 71 of the analyzing device 70 through the scattered light optical fiber cable 45. The spectroscope 71 disperses incident scattered light for each of the plurality of wavelength bands. As shown in FIG. 4, the camera 72 converts a light intensity for each of the plurality of wavelength bands dispersed using the spectroscope 71 into a digital signal and outputs the converted digital signal to the analyzing unit 83 of the computer 80. The analyzing unit 83 analyzes a composition in the fluid G on the basis of a digital signal associated with light for each of the plurality of wavelength bands. The analyzing unit 83 pre-stores a relationship between a wavelength of laser light with which the fluid G is irradiated and an amount of shift of a wavelength of scattered light emitted from each component when the laser light is radiated. The analyzing unit 83 analyzes the component in the fluid G using this relationship. Furthermore, the analyzing unit 83 obtains a concentration of the component in the fluid G on the basis of an intensity of scattered light for each component. When the fluid G is a BFG which is a gas, the analyzing unit 83 obtains a high heating value (HHV) or a low heating value (LHV) of the BFG if necessary.

Figures 3, 4:
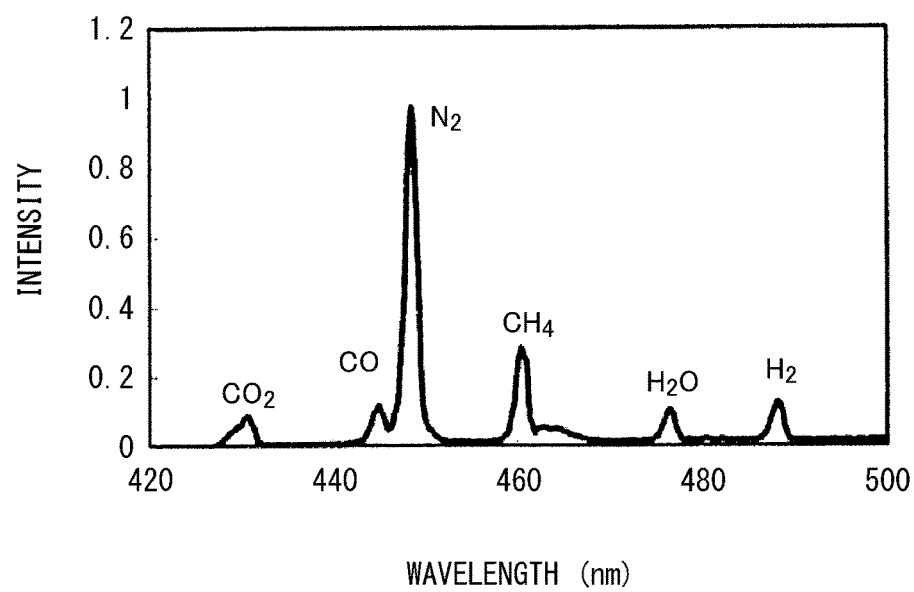
FIG. 3 is an explanatory diagram illustrating an amount of shift of a wavelength of Raman scattered light emitted from each component with respect to a wavelength of excitation light with which a fluid is irradiated and a wavelength of Raman scattered light emitted from each component when the excitation light has a predetermined wavelength.
FIG. 4 is a graph showing a relationship between a wavelength of Raman scattered light emitted from each component when a fluid is irradiated with excitation light and an intensity of each wavelength.

The following Expression (1) is an expression for obtaining a high heating value (HHV) per unit volume of the BFG when the BFG includes carbon dioxide ($CO_2$), carbon monoxide (CO), nitrogen ($N_2$), methane ($CH_4$), water vapor ($H_2O$), or hydrogen ($H_2$) as illustrated in FIG. 4. Furthermore, the following Expression (2) is an expression for obtaining a low heating value (LHV) per unit volume of the BFG in the same case.

[Math. 1]

$$HHV = 3020 \times CCO + 3050 \times CH_2 + 9520 \times CCH_4 \qquad (1)$$

[Math. 2]

$$LHV = 3020 \times CCO + 2570 \times CH_2 + 8550 \times CCH_4 \qquad (2)$$

The HHV is a calorific value (kcal/m$^3$N) in which the heat of condensation of water generated through combustion of the BFG is included as a calorific value. The LHV is a calorific value (kcal/m$^3$N) in which the heat of condensation of water generated through combustion of the BFG is not included as a calorific value. Furthermore, in the Expressions (1) to (8), $CN_2$ is a mole fraction of $N_2$, CCO is a mole fraction of CO, $CCO_2$ is a mole fraction of $CO_2$, $CH_2O$ is a mole fraction of $H_2O$, $CH_2$ is a mole fraction of $H_2$, and $CCH_4$ is a mole fraction of $CH_4$. The mole fraction of each component can be calculated using the following Expressions (3) to (8).

[Math. 3]

$$CN_2 = \frac{1}{1 + \alpha CO \cdot \frac{ICO}{IN_2} + \alpha CO_2 \cdot \frac{ICO_2}{IN_2} + \alpha H_2O \cdot \frac{IH_2O}{IN_2} + \alpha H_2 \cdot \frac{IH_2}{IN_2} + \alpha CH_4 \cdot \frac{ICH_4}{IN_2}} \qquad (3)$$

[Math. 4]

$$CCO = \frac{\alpha CO \cdot \frac{ICO}{IN_2}}{1 + \alpha CO \cdot \frac{ICO}{IN_2} + \alpha CO_2 \cdot \frac{ICO_2}{IN_2} + \alpha H_2O \cdot \frac{IH_2O}{IN_2} + \alpha H_2 \cdot \frac{IH_2}{IN_2} + \alpha CH_4 \cdot \frac{ICH_4}{IN_2}} \qquad (4)$$

[Math. 5]

$$CCO_2 = \frac{\alpha CO_2 \cdot \frac{ICO_2}{IN_2}}{1 + \alpha CO \cdot \frac{ICO}{IN_2} + \alpha CO_2 \cdot \frac{ICO_2}{IN_2} + \alpha H_2O \cdot \frac{IH_2O}{IN_2} + \alpha H_2 \cdot \frac{IH_2}{IN_2} + \alpha CH_4 \cdot \frac{ICH_4}{IN_2}} \qquad (5)$$

[Math. 6]

$$CH_2O = \frac{\alpha H_2O \cdot \frac{IH_2O}{IN_2}}{1 + \alpha CO \cdot \frac{ICO}{IN_2} + \alpha CO_2 \cdot \frac{ICO_2}{IN_2} + \frac{\alpha H_2O \cdot IH_2O}{IN_2} + \alpha H_2 \cdot \frac{IH_2}{IN_2} + \alpha CH_4 \cdot \frac{ICH_4}{IN_2}} \qquad (6)$$

-continued

[Math. 7]
$$CH_2 = \frac{\alpha H_2 \cdot \frac{IH_2}{IN_2}}{1 + \alpha CO \cdot \frac{ICO}{IN_2} + \alpha CO_2 \cdot \frac{ICO_2}{IN_2} + \alpha H_2O \cdot \frac{IH_2O}{IN_2} + \alpha H_2 \cdot \frac{IH_2}{IN_2} + \alpha CH_4 \cdot \frac{ICH_4}{IN_2}} \quad (7)$$

[Math. 8]
$$CCH_4 = \frac{\alpha CH_4 \cdot \frac{ICH_4}{IN_2}}{1 + \alpha CO \cdot \frac{ICO}{IN_2} + \alpha CO_2 \cdot \frac{ICO_2}{IN_2} + \alpha CO_2 \cdot \frac{IH_2O}{IN_2} + \alpha H_2 \cdot \frac{IH_2}{IN_2} + \alpha CH_4 \cdot \frac{ICH_4}{IN_2}} \quad (8)$$

The analyzing unit 83 obtains a relative intensity ICO/IN$_2$ of a carbon monoxide component with respect to a light intensity IN$_2$ of a nitrogen component, a relative intensity ICO$_2$/IN$_2$ of a carbon dioxide component to the light intensity IN$_2$ of the nitrogen component, a relative intensity IH$_2$O/IN$_2$ of a water vapor component to the light intensity IN$_2$ of the nitrogen component, a relative intensity IH$_2$/IN$_2$ of a hydrogen component to the light intensity IN$_2$ of the nitrogen component, and a relative intensity ICH$_4$/IN$_2$ of a methane component to the light intensity IN$_2$ of the nitrogen component from the intensity of the scattered light for each component in the BFG. Subsequently, the analyzing unit 83 obtains the high heating value (HHV) or the low heating value (LHV) of the BFG using the relative intensity of each of the components, Expression (1) or (2) and Expressions (3) to (8). Although Expressions (1) to (8) are the expressions associated with a volume ratio in which H$_2$O is taken into consideration, a calorific value may be obtained using an expression associated with a volume ratio of the gas in which H$_2$O is excluded.

The concentration of the component in the fluid G, the low heating value (LHV), or the like obtained using the analyzing unit 83 is transmitted to the control device 140 of the gas turbine plant. As described above, the control device 140 controls the degree of opening of the circulation amount adjustment valve 137, the degree of opening of the inlet guide vane 113, and the like on the basis of data transmitted from the analyzing unit 83, that is, the analysis result.

The laser light which has passed through the fluid G is incident on the light receiving prism 33 through the laser receiving window 32. An optical axis of the laser light is perpendicularly bent through the light receiving prism 33. The laser light whose optical axis is bent is condensed through the light receiving surface 36 of the laser receiving optical fiber cable 35 using the condensing optical system 34. The light receiving determination unit 66 determines the intensity of the laser light incident on the laser receiving optical fiber cable 35.

The intensity of laser light determined by the emitted light determination unit 65 and the intensity of laser light determined by the light receiving determination unit 66 are transmitted to the determination unit 82 of the computer 80. As described above, the determination unit 82 determines a state of the scattered light acquisition head 12 in accordance with the intensity of the laser light determined by each of the determination units 65 and 66. The determination result of the determination unit 82 is transmitted to the control device 140 of the gas turbine plant. The control device 140 causes the determination result of the determination unit 82 to be displayed if necessary.

The laser light oscillated from the heating laser oscillator 62 is guided into the cavity 51 of the light shielding member 50 through the heating optical fiber cable 55. The laser light is repeatedly irregularly reflected by the inner surface of the cavity in the cavity 51 of the light shielding member 50. As a result, light energy of the laser light is converted into heat energy using which the light shielding member 50 and the scattered light window 42 in contact with the light shielding member 50 are heated. That is to say, in this embodiment, the scattered light window 42 is heated using the energy of the laser light.

Also, since the laser light from the heating optical fiber cable 55 is guided into the cavity 51 of the light shielding member 50 in this embodiment, it is possible to irradiate the light shielding member 50 with all of the laser light and it is possible to increase the efficiency of converting the light energy of the laser light into heat energy.

Incidentally, when foreign matter is present in the fluid G, the inner surface 22i of the laser emission window 22 which partitions the inside of the head casing 13 and the flow path of the fluid G, the inner surface 32i of the laser receiving window 32, and the inner surface 42i of the scattered light window 42 become contaminated by the foreign matter. For example, when the fluid G is one of a blast furnace gas (BFG) and a coke oven gas (COG) or a mixed gas of BFG and COG, foreign matter such as ash becomes present in the fluid G.

An intensity of the Raman scattered light is much smaller than an intensity of the laser light with which the fluid G is irradiated. For this reason, if the inner surface 42i of the scattered light window 42 is dirty, the foreign matter hinders the composition analysis of the fluid G based on the scattered light. Thus, in this embodiment, as described above, foreign matter adhered to the inner surface 42i of the scattered light window 42 is removed and adhering of foreign matter to the inner surface 42i of the scattered light window 42 is prevented by heating the scattered light window 42.

As a method of heating the scattered light window 42, there is a method of heating the scattered light window 42 wire by bringing the heating wire into contact with or into proximity to the scattered light window 42 and causing a current to pass through the heating wire. In this way, when the heating wire is brought into contact with or into proximity to the scattered light window 42 if the fluid G is a combustible gas such as a BFG or a COG, explosion-proof treatment needs to be applied to a heating wire or an electric cable through which a current is supplied to the heating wire. On the other hand, since electricity is not used to heat the scattered light window 42 in this embodiment, it is not necessary to apply explosion-proof treatment to a component necessary for heating the scattered light window 42, specifically, the heating optical fiber cable 55 and the light heat shield member. Thus, in this embodiment, it is possible to save the cost of the explosion-proof treatment for the component necessary for heating the scattered light window 42.

In this embodiment, as described above, the light receiving surface 46 of the scattered light receiving device 44 is arranged at a position in which the light receiving surface 46 is separated from the optical axis Aw in the fluid in the radial direction Dr within the range Rw in which the optical path of the laser light in the fluid G is present in the optical axis direction Da. In other words, in this embodiment, the light receiving surface 46 of the scattered light receiving device 44 is arranged at a position in which the light receiving surface 46 is separated from a scattered light generation region Rrs in the fluid G in a direction in which the light receiving surface 46 is perpendicular to the optical axis Aw in the fluid. For this reason, in this embodiment, the light receiving surface 46 of the scattered light receiving device 44 can be brought into proximity to the scattered light generation region Rrs in the fluid G. Moreover, in this embodiment, the inner surface 42i and the outer surface 42o of the scattered light window 42 and the light receiving surface 46 of the scattered light receiving device 44 are parallel to the optical axis Aw in the fluid. Thus, it is possible to shorten an optical path length of the scattered light from the scattered light generation region Rrs to the light receiving surface 46 of the scattered light receiving device 44. Therefore, in this embodiment, it is possible to reduce sizes of the Raman scattered light acquisition device 11 and the composition analysis device 10 including the Raman scattered light acquisition device 11.

Furthermore, in this embodiment, the light receiving surface 46 of the scattered light receiving device 44 can be brought into proximity to the scattered light generation region Rrs in the fluid G. Thus, the light receiving surface 46 of the scattered light receiving device 44 can receive Raman scattered light with little attenuation. For this reason, in this embodiment, the condensing optical system configured to condense the scattered light which has passed through the scattered light window 42 can be omitted. To be specific, in this embodiment, the condensing optical system can be omitted by setting a distance from the optical axis Aw in the fluid to the light receiving surface 46 of the scattered light receiving device 44 in a radial direction (a direction perpendicular to the optical axis in the fluid) to be equal to or less than a distance in which an amount of Raman scattered light to be received by the scattered light receiving device 44 is a minimum amount of light in which the composition of the fluid G can be analyzed using the analyzing device 70. Thus, in this embodiment, also from this point of view, it is possible to reduce sizes of the Raman scattered light acquisition device 11 and the composition analysis device 10 including the Raman scattered light acquisition device 11.

In addition, in this embodiment, as described above, all of the emission surface optical axis Ao of the emission optical fiber cable 25, the light receiving surface optical axis Ai of the laser receiving optical fiber cable 35, and the light receiving surface optical axis Ars of the scattered light optical fiber cable 45 are parallel to each other and are perpendicular to the optical axis Aw in the fluid. Thus, in this embodiment, it is possible to minimize widths in the optical axis direction Da of the Raman scattered light acquisition device 11 and the composition analysis device 10 including the Raman scattered light acquisition device 11.

Second Embodiment

Figure 6:
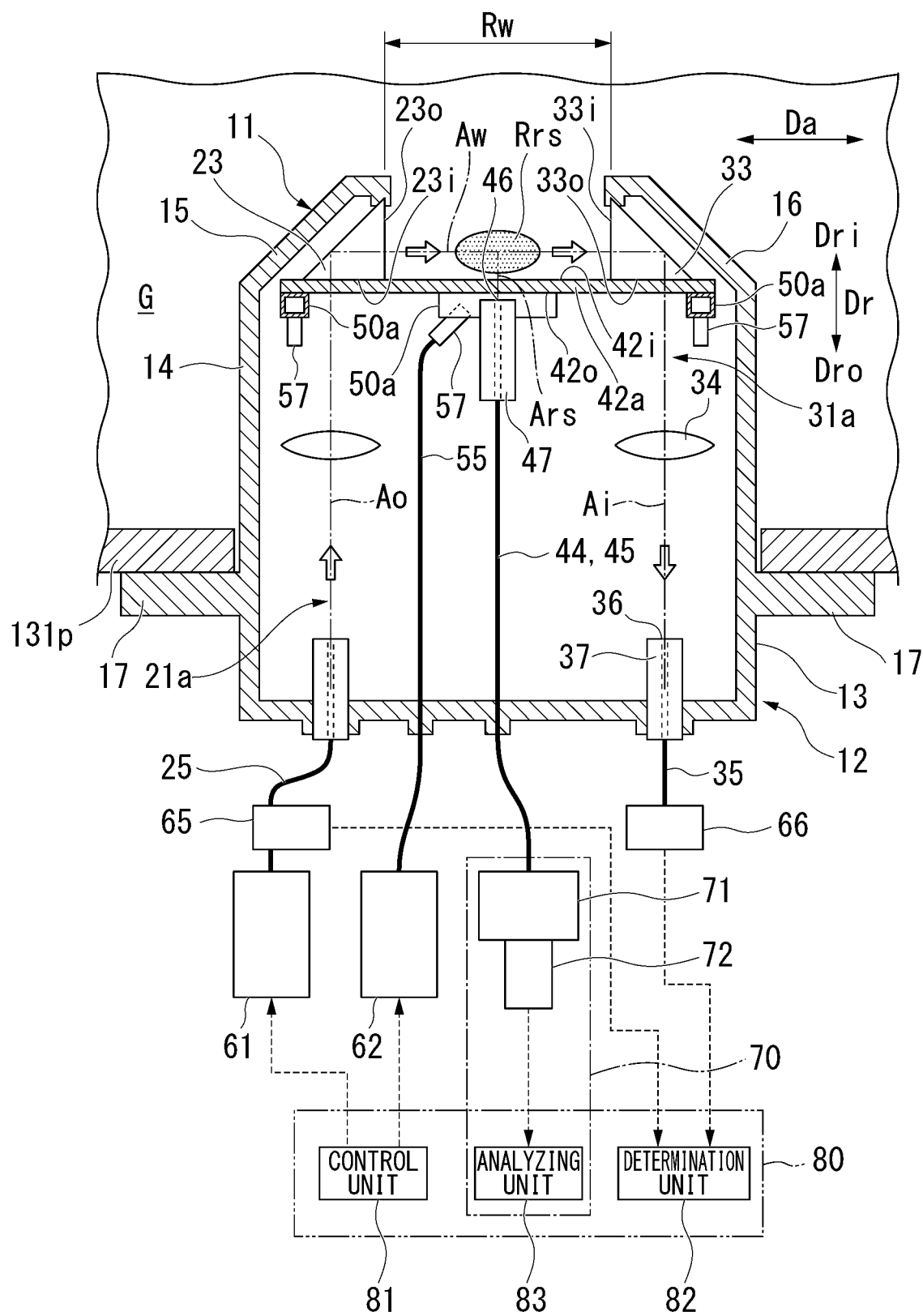
FIG. 6 is a schematic diagram illustrating a constitution of a composition analysis device according to a second embodiment of the present invention.

A second embodiment of the composition analysis device associated with the present invention will be described with reference to FIG. 6.

The composition analysis device in this embodiment is different from the composition analysis device in the first embodiment in that the emission prism 23 and the light receiving prism 33 are in contact with the fluid G and a plurality of light shielding members 50a are provided but the other points are basically the same as those of the composition analysis device in the first embodiment.

The scattered light window 42a in this embodiment is arranged at a position in which the scattered light window 42a is separated from the optical axis Aw in the fluid in the radial direction Dr, as in the scattered light window 42a in the first embodiment. Also in the scattered light window 42a in this embodiment, both of the inner surface 42i which defines the flow path of the fluid G and the outer surface 42o which is a surface in the scattered light window 42 opposite to the inner surface 42i are parallel to the optical axis Aw in the fluid. Here, the length of the scattered light window 42a in this embodiment in the optical axis direction Da is longer than that of the scattered light window 42 in the first embodiment. To be specific, the scattered light window 42a in this embodiment extends in the optical axis direction Da to a position farther than a position of the emission surface optical axis Ao of the emission optical fiber cable 25 with reference to the light receiving surface optical axis Ars of the scattered light optical fiber cable 45. Furthermore, the scattered light window 42a in this embodiment extends in the optical axis direction Da to a position farther than a position of the light receiving surface optical axis Ai of the laser receiving optical fiber cable 35 with reference to the light receiving surface optical axis Ars of the scattered light optical fiber cable 45. That is to say, the scattered light window 42a in this embodiment is also present in the optical axis direction Da at a position of the emission surface optical axis Ao of the emission optical fiber cable 25 and a position of the light receiving surface optical axis Ai of the laser receiving optical fiber cable 35. For this reason, the scattered light passes through the scattered light window 42a in this embodiment within the range Rw in which the optical path of the laser light in the fluid G is present in the optical axis direction Da and the scattered light window 42a is subjected to a process of reflecting the laser light. In addition, the scattered light window 42a is not subjected to a process of reflecting laser light and the laser light passes through the scattered light window 42a outside of the range Rw.

The emission optical system 21a in this embodiment has the emission optical fiber cable 25 through which laser light from the analyzing laser oscillator 61 passes, a part of the scattered light window 42a, and the emission prism (the changer) 23 which changes a direction of laser light which is emitted from the emission optical fiber cable 25 and has passed through the scattered light window 42a. An incident surface 23i of the emission prism 23 is in contact with the outer surface 42o of the scattered light window 42a. On the other hand, an emission surface 23o of the emission prism 23 forms a surface which defines the flow path of the fluid G. For this reason, the emission optical system 21a in this embodiment does not have the laser emission window 22.

The laser light receiving optical system (the excitation light receiving optical system) 31a includes the light receiving prism 33 which changes a direction of laser light, a part of the scattered light window 42a, the laser receiving optical fiber cable 35, and the condensing optical system 34 which condenses laser light which has passed through the light receiving prism 33 and the scattered light window 42a to the light receiving surface 36 of the laser receiving optical fiber cable 35. The incident surface 23i of the light receiving prism 33 forms a surface which defines the flow path of the fluid G. For this reason, the laser light receiving optical system 31a in this embodiment does not have the laser receiving window 32. The emission surface 33o of the light receiving prism 33 is in contact with the outer surface 42o of the scattered light window 42a.

As described above, since the laser emission window 22 and the laser receiving window 32 in the first embodiment are not provided in this embodiment, it is possible to simplify a device and to minimize the production costs thereof.

In the first embodiment, one light shielding member 50 is provided and an outer shape thereof is annular. On the other hand, in this embodiment, as described above, a plurality of light shielding members 50a are provided. All of the plurality of light shielding members 50a are adhered to the outer surface 42o of the scattered light window 42a with an adhesive or the like. The light shielding member 50 is formed of a member through which laser light or Raman scattered light is not transmitted, which easily absorbs the energy of the laser light or the Raman scattered light, and which has good thermal conductivity. The plurality of light shielding members 50a are separated from each other in a circumferential direction with respect to the light receiving surface optical axis Ars of the scattered light optical fiber cable 45. The sleeve 57 of the heating optical fiber cable 55 is attached to each of the plurality of light shielding members 50a, as in the first embodiment. The heating laser oscillator 62 is connected to each heating optical fiber cable 55.

As described above, one light shielding member may be provided or a plurality of light shielding members may be provided.

Also, in this embodiment, the laser emission window 22 and the laser receiving window 32 are in contact with the scattered light window 42a. Thus, if the scattered light window 42a is heated using the energy of the laser light oscillated from the heating laser oscillator 62, the emission prism 23 and the light receiving prism 33 are also heated. For this reason, it is possible to remove foreign matter in the fluid G adhered to the emission surface 23o of the emission prism 23 and the incident surface 33i of the light receiving prism 33 and to prevent adhering of foreign matter to the emission surface 23o of the emission prism 23 and the incident surface 33i of the light receiving prism 33.

Modified Example and the Like

In the embodiment described above, the fact that B is perpendicular to A means not only that an angle of B with respect to A is 90° but also that the angle of B with respect to A is about 88° to 92° and B is substantially perpendicular to A. Furthermore, the fact that A and B are parallel to each other means not only that an angle of B with respect to A is 0° but also that the angle of B with respect to A is about −2° to +2° and B is substantially parallel to A.

In the above embodiment, the laser light receiving optical system (the excitation light receiving optical system) 31 or 31a has the condensing optical system 34. However, if an intensity of the laser light incident on the laser light receiving optical system 31 is not extremely smaller than an intensity of the laser light from the analyzing laser oscillator 61 which is a light emission unit, the condensing optical system 34 may be omitted.

The laser light receiving optical system (the excitation light receiving optical system) 31 or 31a in the above embodiment is an optical system provided for determining an abnormality of the scattered light acquisition head 12. Thus, when it is not necessary to determine an abnormality of the scattered light acquisition head 12, the laser light receiving optical system (the excitation light receiving optical system) 31 or 31a may be omitted.

The changer in the above embodiment is the emission prism 23 or the light receiving prism 33. However, the changer may be a mirror.

The scattered light receiving device 44 in the above embodiment does not have a condensing optical system. However, the scattered light receiving device 44 may have a condensing optical system.

The fluid G to be analyzed in the above embodiment is a gas G which is unmixed BFG. However, the fluid G to be analyzed may be unmixed COG, a mixture of a BFG and a COG, or a mixture of a BFG, a COG, and a LDG. Furthermore, the fluid G to be analyzed may be another fuel gas, for example, natural gas, biogas, or the like. In addition, the fluid G to be analyzed may not be a fuel gas.

INDUSTRIAL APPLICABILITY

According to an aspect of the present invention, it is possible to reduce a size of a Raman scattered light acquisition device.

REFERENCE SIGNS LIST

10 Composition analysis device
11 Raman scattered light acquisition device
12 Scattered light acquisition head
13 Head casing
14 Main body section
15 First protrusion section
16 Second protrusion section
17 Attachment flange
21, 21a Emission optical system
22 Laser emission window
22i Inner surface
22o Outer surface
23 Emission prism (changer)
23i Incident surface
23o Emission surface
25 Emission optical fiber cable
26 Emission surface
27 Sleeve
31, 31a Laser light receiving optical system (excitation light receiving optical system)
32 Laser receiving window
32i Inner surface
32o Outer surface
33 Light receiving prism (changer)
33i Incident surface
33o Emission surface
34 Condensing optical system
35 Laser receiving optical fiber cable
36 Light receiving surface
37 Sleeve
42, 42a Scattered light window
42i Inner surface
42o Outer surface
44 Scattered light receiving device
45 Scattered light optical fiber cable
46 Light receiving surface
47 Sleeve
50 Light shielding member
51 Cavity
55 Heating optical fiber cable
57 Sleeve
61 Analyzing laser oscillator (light emission unit)
62 Heating laser oscillator
65 Emitted light determination unit
66 Light receiving determination unit
70 Analyzing device
71 Spectroscope 72 Camera
80 Computer
81 Control unit
82 Determination unit
83 Analyzing unit
110 Gas turbine
111 Air compressor
112 Intake amount adjuster
115 Combustor
116 Turbine
120 Electric generator
121 Gas compressor
122 Intake gas amount adjuster (fuel adjustment valve)
126 Speed reducer
127 Electrostatic precipitator
131 BFG line
132 COG line
133 Low-pressure fuel gas line
133$p$ Pipe
134 High-pressure fuel gas line
135 Fuel gas circulation line
136 COG adjustment valve
137 Circulation amount adjustment valve (fuel adjustment valve)
138 Gas cooler
140 Control device
G Fluid (fuel gas)
Rrs Scattered light generation region
Ao Emission surface optical axis of emission optical fiber cable
Ai Light receiving surface optical axis of laser receiving optical fiber cable
Ars Light receiving surface optical axis of scattered light optical fiber cable
Aw Optical axis in fluid
Da Optical axis direction
Dr Radial direction
Dri Radially inward side
Dro Radially outward side

The invention claimed is:

1. A Raman scattered light acquisition device, comprising:
an emission optical system configured to guide excitation light from a light emission unit into a fluid;
a scattered light window configured to define a part of a flow path of the fluid and through which Raman scattered light from the fluid irradiated with the excitation light passes; and
a scattered light receiving device having a light receiving surface for receiving the Raman scattered light which has passed through the scattered light window,
wherein the scattered light window and the light receiving surface of the scattered light receiving device are arranged at positions in which the scattered light window and the light receiving surface are separated from an optical axis in the fluid in a radial direction which is a direction perpendicular to the optical axis in the fluid within a range in which an optical path of the excitation light in the fluid is present in an optical axis direction in which the optical axis in the fluid which is an optical axis of the excitation light in the fluid extends, and
the light receiving surface faces a radially inward side which is a side in proximity to the optical axis in the fluid in the radial direction, and
the Raman scattered light acquisition device further comprises:
a light shielding member through which the excitation light and the Raman scattered light do not pass; and
a heating optical fiber cable for irradiating the light shielding member with excitation light,
wherein the light shielding member is in contact with an outer surface of the scattered light window on the light receiving surface side.

2. The Raman scattered light acquisition device according to claim 1, wherein a light receiving surface optical axis, which is an optical axis in the light receiving surface of the scattered light receiving device, is perpendicular to the optical axis in the fluid.

3. The Raman scattered light acquisition device according to claim 1, wherein an inner surface in the scattered light window which is configured to define a flow path of the fluid and an outer surface opposite to the inner surface are both parallel to the optical axis in the fluid.

4. The Raman scattered light acquisition device according to claim 1, wherein the emission optical system includes an emission optical fiber cable through which the excitation light from the light emission unit passes and a changer which is configured to change a direction of the excitation light emitted from the emission optical fiber cable,
an emission surface optical axis which is an optical axis in an emission surface of the emission optical fiber cable which emits the excitation light extends in a direction intersecting the optical axis in the fluid,
the emission surface of the emission optical fiber cable and the changer are arranged on one side in the optical axis direction with reference to the light receiving surface of the scattered light receiving device, and
the changer is configured to cause the optical axis of the excitation light emitted from the emission optical fiber cable to coincide with the optical axis in the fluid.

5. The Raman scattered light acquisition device according to claim 4, wherein the emission surface optical axis is perpendicular to the optical axis in the fluid.

6. The Raman scattered light acquisition device according to claim 1, wherein a cavity which extends along the outer surface of the scattered light window is formed inside the light shielding member, and
the heating optical fiber cable is configured to emit the excitation light into the cavity of the light shielding member.

7. The Raman scattered light acquisition device according to claim 1, comprising:
an excitation light receiving optical system which is configured to receive the excitation light from the emission optical system; and
a determination unit which is configured to determine an abnormality of an excitation light optical system constituted of a plurality of members through which the excitation light passes in accordance with a difference between a light intensity of the excitation light from the light emission unit and a light intensity of the excitation light received by the excitation light receiving optical system.

8. The Raman scattered light acquisition device according to claim 7, wherein the excitation light receiving optical system is arranged on a side opposite to the emission optical system in the optical axis direction with reference to the light receiving surface of the scattered light receiving device.

9. The Raman scattered light acquisition device according to claim 1, comprising:
the light emission unit.

10. A composition analysis device, comprising:
the Raman scattered light acquisition device according to claim 1; and an analyzing device which is configured to analyze a composition of the fluid on the basis of an output from the scattered light receiving device.

11. The composition analysis device according to claim 10, wherein a distance in the radial direction from the optical axis in the fluid to the light receiving surface of the scattered light receiving device is equal to or less than a distance in which an amount of the Raman scattered light to be received by the scattered light receiving device is a minimum amount of light in which the analyzing device is able to analyze the composition of the fluid.

12. A gas turbine plant, comprising:
the composition analysis device according to claim 10;
a fuel gas line through which a fuel gas as the fluid flows;
a fuel adjustment valve which is configured to adjust a flow rate of the fuel gas flowing through the fuel gas line;
a gas turbine configured to be driven through combustion of the fuel gas from the fuel gas line; and
a control device which is configured to instruct a degree of opening of the fuel adjustment valve,
wherein the Raman scattered light acquisition device is attached to the fuel gas line,
the analyzing device is configured to analyze a composition of the fuel gas flowing in the fuel gas line, and
the control device is configured to determine the degree of opening of the fuel adjustment valve in accordance with an analysis result in the analyzing device and instruct the degree of opening to the fuel adjustment valve.

13. A gas turbine plant comprising:
a fuel gas line through which a fuel gas as the fluid flows;
a fuel adjustment valve configured to adjust a flow rate of the fuel gas flowing through the fuel gas line;
a gas turbine configured to be driven through combustion of the fuel gas from the fuel gas line;
a control device which is configured to instruct a degree of opening of the fuel adjustment valve; and
a composition analysis device comprising:
i) a Raman scattered light acquisition device attached to the fuel gas line, the Raman scattered light acquisition device including:
an emission optical system configured to guide excitation light from a light emission unit into a fluid;
a scattered light window configured to define a part of a flow path of the fluid and through which Raman scattered light from the fluid irradiated with the excitation light passes; and
a scattered light receiving device having a light receiving surface for receiving the Raman scattered light which has passed through the scattered light window,
wherein the scattered light window and the light receiving surface of the scattered light receiving device are arranged at positions in which the scattered light window and the light receiving surface are separated from an optical axis in the fluid in a radial direction which is a direction perpendicular to the optical axis in the fluid within a range in which an optic al path of the excitation light in the fluid is present in an optical axis direction in which the optical axis in the fluid which is an optical axis of the excitation light in the fluid extends, and the light receiving surface faces a radially inward side which is a side in proximity to the optical axis in the fluid in the radial direction; and
ii) an analyzing device configured to analyze a composition of the fluid on the basis of an output from the scattered light receiving device,
wherein the analyzing device is configured to analyze a composition of the fuel gas flowing in the fuel gas line, and
the control device is configured to determine the degree of opening of the fuel adjustment valve in accordance with an analysis result in the analyzing device and instruct the degree of opening to the fuel adjustment valve.

* * * * *